United States Patent
Subramaniyam

(10) Patent No.: US 9,725,649 B2
(45) Date of Patent: *Aug. 8, 2017

(54) AMINE AND NITROXIDE BASED ADDITIVE COMPOSITION FOR CONTROL AND INHIBITION OF POLYMERIZATION OF STYRENE, AND METHOD OF USE THEREOF

(71) Applicant: Dorf Ketal Chemicals (India) Private Limited, Mumbai (IN)

(72) Inventor: Mahesh Subramaniyam, Mumbai (IN)

(73) Assignee: Dorf Ketal Chemicals (India) Private Limited, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/362,047

(22) PCT Filed: Nov. 21, 2012

(86) PCT No.: PCT/IN2012/000758
§ 371 (c)(1),
(2) Date: May 30, 2014

(87) PCT Pub. No.: WO2013/105113
PCT Pub. Date: Jul. 18, 2013

(65) Prior Publication Data
US 2014/0364660 A1 Dec. 11, 2014

(30) Foreign Application Priority Data
Dec. 2, 2011 (IN) .................. 3383/MUM/2011

(51) Int. Cl.
*C07C 7/20* (2006.01)
*C09K 15/20* (2006.01)
*C08F 2/40* (2006.01)
*C08K 5/17* (2006.01)
*C08K 5/32* (2006.01)

(52) U.S. Cl.
CPC ............ *C09K 15/20* (2013.01); *C07C 7/20* (2013.01); *C08F 2/40* (2013.01); *C08K 5/17* (2013.01); *C08K 5/32* (2013.01); *C08F 2438/02* (2013.01)

(58) Field of Classification Search
CPC ........................................... C07C 7/20
USPC ..................................... 585/5, 952
See application file for complete search history.

(56) References Cited

U.S. PATENT DOCUMENTS

| 4,633,026 A | 12/1986 | Kolich |
| 5,254,760 A | 10/1993 | Winter et al. |
| 5,290,888 A * | 3/1994 | Gatechair et al. ............ 526/83 |
| 5,910,232 A * | 6/1999 | Hyde et al. .................. 203/9 |
| 6,403,850 B1 * | 6/2002 | Benage et al. ............... 585/5 |
| 6,673,879 B2 * | 1/2004 | Shahid ....................... 526/82 |

FOREIGN PATENT DOCUMENTS

| FR | 2632638 A1 | 12/1989 |
| IN | 3383MUM2011 | 12/2011 |
| WO | 2013105113 A1 | 7/2013 |
| WO | 2013105113 A4 | 7/2013 |

OTHER PUBLICATIONS

Foreign communication from the priority application—International Search Report and Written Opinion, PCT/IN2012/000758, May 16, 2013, 6 pages.
Foreign communication from the priority application—International Preliminary Report on Patentability, PCT/IN2012/000758, Dec. 11, 2013, 20 pages.

* cited by examiner

*Primary Examiner* — Ellen McAvoy
(74) *Attorney, Agent, or Firm* — Conley Rose, P.C.; Rodney B. Carroll

(57) ABSTRACT

The present invention relates to additive composition for controlling and inhibition of polymerization of aromatic vinyl monomers including styrene comprising (a) one or more of nitroxide (i.e. nitroxyl) compounds, and characterized in that the said composition further comprises one or more of (b) aliphatic amines selected from a group comprising tertiary amines, secondary amines and primary amines. In one embodiment, the present invention also relates to method of use of presently provided composition. In another embodiment, the present invention also relates to method of controlling and inhibiting polymerization of aromatic vinyl monomers including styrene by employing presently provided composition. In still another embodiment, the present invention also relates to method of preparation of presently provided composition.

33 Claims, No Drawings

AMINE AND NITROXIDE BASED ADDITIVE COMPOSITION FOR CONTROL AND INHIBITION OF POLYMERIZATION OF STYRENE, AND METHOD OF USE THEREOF

CROSS-REFERENCE TO RELATED APPLICATIONS

This application is a filing under 35 U.S.C. 371 of International Application No. PCT/IN2012/000758 filed Nov. 21, 2012, entitled "Amine and Nitroxide Based Additive Composition for Control and Inhibition of Polymerization of Styrene, and Method of Use Thereof," which claims priority to Indian Patent Application No. 3383/MUM/2011 filed Dec. 2, 2011, which applications are incorporated by reference herein in their entirety.

FIELD OF THE INVENTION

The present invention relates to amine and nitroxide based additive composition for control and inhibition of polymerization of aromatic vinyl monomers, wherein aromatic vinyl monomer include styrene.

In one embodiment, the present invention relates to use of amine and nitroxide based additive composition of present invention to control and inhibit polymerization of aromatic vinyl monomers including styrene.

In another embodiment, the present invention relates to method of preparation of amine and nitroxide based additive composition of present invention for control and inhibition of polymerization of aromatic vinyl monomers including styrene.

In still another embodiment, the present invention relates to method of controlling and inhibiting polymerization of aromatic vinyl monomers including styrene by employing amine and nitroxide based additive composition of present invention.

BACKGROUND OF THE INVENTION

The polymerization of aromatic vinyl monomers including styrene during processing is a matter of concern, because it causes formation of unwanted polymers and results in loss of yield of end product and makes the process un-economical.

In the art use of inhibitors and retarders, and combination thereof to overcome problem of polymerization of styrene has been reported.

The problem of using the inhibitors alone is that these are to be added continuously or at regular interval, because once they are consumed, the polymerization will re-start.

The problem of using the retarders alone is that these are not very effective to reduce polymerization of styrene to a level of substantial inhibition or to the acceptable level of inhibition.

The prior art [U.S. Pat. No. 5,254,760 (US '760)] discloses the polymerization inhibition of vinyl monomers using a combination of nitroxides (i.e. nitroxyl compounds) including 1 oxyl-2,2,6,6, tetramethylpiperidin-4-ol (4HT) and aromatic nitro compounds including dinitro-butylphenol [re abstract, Col. 3, lines 26-32; Col. 4, lines 1-2, 12 of US '760] as the polymerization inhibitor.

The US'760 discloses and teaches use of combination of nitroxides (i.e. nitroxyl) compound and aromatic nitro compound. The US'760 discloses and teaches against the use of either of nitroxides (i.e. nitroxyl) compound or of aromatic nitro compound [Re Col. 5, lines 50-56; Col. 6, lines 10-14 and 42-46; Col. 7, lines 36-41 of US'760].

However, the aromatic nitro compounds including DNBP are to be used in higher amounts and/or are also known for their toxic nature for human exposure [re Col. 1, lines 64-68 of US'760].

Therefore, the industry is aiming for additive composition wherein the aromatic nitro compounds can be avoided. Any effort to avoid consumption of aromatic nitro compounds will lessen the problem of industry.

NEED OF THE INVENTION

Therefore, there is still a need of an effective additive composition and method of its use and preparation, and method of controlling and inhibiting polymerization of vinyl aromatic monomers by employing said composition, wherein the additive composition is not only suitable for substantial control and inhibition of polymerization of aromatic vinyl monomers including styrene, but also does not comprise aromatic nitro compounds.

SUMMARY OF THE INVENTION

Therefore, the present invention aims at providing a solution to above-described existing industrial problems by providing effective additive composition and method of its use and preparation, and method of controlling and inhibiting polymerization of vinyl aromatic monomers, wherein the additive composition is not only suitable for substantial control and inhibition of polymerization of aromatic vinyl monomers including styrene, but also does not comprise aromatic nitro compounds.

In addition to above aim, the present invention also aims at providing an effective additive composition and method of its use and preparation, and method of controlling and inhibiting polymerization of vinyl aromatic monomers, wherein the additive composition is not only suitable for substantial control and inhibition of polymerization of aromatic vinyl monomers including styrene, but also comprises reduced or minimized amount of nitroxides (i.e. nitroxyl) compounds.

OBJECTS OF THE INVENTION

Accordingly, the main object of present invention is to provide an effective additive composition and method of its use and preparation, and method of controlling and inhibiting polymerization of vinyl aromatic monomers, wherein the additive composition is not only suitable for substantial control and inhibition of polymerization of aromatic vinyl monomers including styrene, but also does not comprise aromatic nitro compounds.

Another main object of present invention is to provide an effective additive composition and method of its use and preparation, and method of controlling and inhibiting polymerization of vinyl aromatic monomers, wherein the additive composition is not only suitable for substantial control and inhibition of polymerization of aromatic vinyl monomers including styrene, but also comprises reduced or minimized amount of nitroxides (i.e. nitroxyl) compounds.

This is also an object of present invention to provide an effective additive composition and method of its use and preparation, and method of controlling and inhibiting polymerization of vinyl aromatic monomers, wherein the additive composition comprises reduced or minimized amount of one or more of nitroxides (i.e. nitroxyl) compounds, and does not comprise aromatic nitro compounds, and is still suitable for substantial control and inhibition of polymerization of aromatic vinyl monomers including styrene, and is still required in relatively lower dosage as compared to dosage of nitroxides (i.e. nitroxyl) compounds alone for achieving the same or better acceptable level of control and inhibition of polymerization of aromatic vinyl monomers including styrene.

This is also an object of present invention to provide an effective additive composition and method of its use and preparation, and method of controlling and inhibiting polymerization of vinyl aromatic monomers, wherein the additive composition comprises one or more of amines and reduced or minimized amount of one or more of nitroxides (i.e. nitroxyl) compounds, and does not comprise aromatic nitro compounds, and is still suitable for substantial control and inhibition of polymerization of aromatic vinyl monomers including styrene, and is still required in relatively lower dosage as compared to dosage of nitroxides (i.e. nitroxyl) compounds alone for achieving the same or better acceptable level of control and inhibition of polymerization of aromatic vinyl monomers including styrene, and wherein the amine is aliphatic amine.

The present invention particularly aims at providing an effective additive composition and method of its use and preparation, and method of controlling and inhibiting polymerization of vinyl aromatic monomers, wherein the additive composition comprises one or more of amines and reduced or minimized amount of one or more of nitroxides (i.e. nitroxyl) compounds, and does not comprise aromatic nitro compounds, and is still suitable for substantial control and inhibition of polymerization of aromatic vinyl monomers including styrene, and is still required in relatively lower dosage as compared to dosage of nitroxides (i.e. nitroxyl) compounds alone for achieving the same or better acceptable level of control and inhibition of polymerization of aromatic vinyl monomers including styrene, and wherein the amine is aliphatic amine, which is selected from a group comprising tertiary amines, secondary amines and primary amines, preferably the amine is tertiary amine, and therefore, the composition of present invention is not only economical, but is also environment friendly.

The present invention also aims at improving the performance of nitroxide (i.e. nitroxyl) compounds at a wider range of temperature including the higher temperature and in presence of air, wherein the composition further comprises one or more aliphatic amines.

Other objects and advantages of present invention will become more apparent from the following description when read in conjunction with examples, which are not intended to limit scope of present invention.

DETAILED DESCRIPTION OF THE INVENTION

With aim to overcome above-described problems of prior art and to achieve above-described objects of the invention, the inventor has found that when an aliphatic amine is added to composition consisting of nitroxide (i.e. nitroxyl) compounds even without aromatic nitro compounds, then not only polymerization controlling and inhibiting efficiency of nitroxides is substantially improved, but polymerization of aromatic vinyl monomers including styrene, surprisingly and unexpectedly, is also controlled and inhibited to the acceptable level at substantially reduced dosages of composition comprising one or more of nitroxide compounds and one or more of aliphatic amine compounds, which makes the composition economical as well as environment friendly.

With aim to overcome above-described problems of prior art and to achieve above-described objects of the invention, the inventor has found that when one or more of aliphatic tertiary amines, or aliphatic tertiary amines containing one or more hydroxyl groups or one or more of secondary amines or one or more of primary amines or mixture thereof is added to composition consisting of one or more of nitroxide (i.e. nitroxyl) compounds without aromatic nitro compounds, then not only polymerization controlling and inhibiting efficiency of nitroxides is substantially improved, but polymerization of aromatic vinyl monomers including styrene, surprisingly and unexpectedly, is also controlled and inhibited to the acceptable level at substantially reduced dosages of composition comprising nitroxide and aliphatic amine compounds, which makes the composition economical as well as environment friendly.

Accordingly, the present invention relates to additive composition for controlling and inhibition of polymerization of aromatic vinyl monomers including styrene comprising:
(a) one or more of nitroxides (i.e. nitroxyls) compounds; and characterized in that the said composition further comprises one or more of
(b) aliphatic amines selected from a group comprising tertiary amines, secondary amines and primary amines, preferably the amine is tertiary amine.

Accordingly, in one embodiment, the present invention relates to additive composition for controlling and inhibition of polymerization of aromatic vinyl monomers including styrene comprising:
(a) one or more of nitroxides (i.e. nitroxyls) compounds; and characterized in that the said composition further comprises one or more of
(b) tertiary amines.

Accordingly, in another embodiment, the present invention relates to additive composition for controlling and inhibition of polymerization of aromatic vinyl monomers including styrene comprising:
(a) one or more of nitroxides (i.e. nitroxyls) compounds; and characterized in that the said composition further comprises one or more of
(b) amines selected from a group consisting of primary amines and secondary amines.

In accordance with present invention, the aliphatic amine is an aliphatic tertiary amine, which contains one or more hydroxyl groups in the alkyl chain of the tertiary amine, preferably it contains three hydroxyl groups in the alkyl chain of the tertiary amine, more preferably the hydroxyl groups are hydroxyalkyl groups.

In accordance with one of the most preferred embodiments of the present invention, the said amine is hydroxyl alkyl tertiary amine.

In accordance with one of the preferred embodiments of the present invention, the said amine is ethylene oxide treated amine.

In accordance with one of the preferred embodiments of the present invention, the said amine is propylene oxide treated amine.

In accordance with one of the preferred embodiments of the present invention, the said amine is tertiary alkyl amine.

In accordance with one of the preferred embodiments of the present invention, the said amine is mixture of one or more of hydroxyl alkyl tertiary amines, ethylene oxide treated amines, propylene oxide treated amines, tertiary alkyl amines.

In accordance with one of the most preferred embodiments of the present invention, the said hydroxyl alkyl tertiary amine is tris(2-hydroxypropyl)amine (TIPA).

In accordance with one of the preferred embodiments of the present invention, the said ethylene oxide treated amine is N,N,N',N'-Tetrakis(2-hydroxyethyl)ethylene-diamine) (THEED).

In accordance with one of the preferred embodiments of the present invention, the said propylene oxide treated amine is N,N,N',N'-Tetrakis(2-hydroxypropyl)ethylene-diamine) (Quadrol).

In accordance with one of the preferred embodiments of the present invention, the said hydroxyl alkyl tertiary amine is triethanolamine (TEA).

In accordance with one of the preferred embodiments of the present invention, the said tertiary alkyl amine is Tris [N-butylamine] (TBA).

In accordance with one of the embodiments of the present invention, the said primary amine is selected from a group comprising hydroxyl alkyl primary amine and alkyl primary amine.

In accordance with one of the embodiments of the present invention, the said secondary amine is alkyl secondary amine.

In accordance with one of the embodiments of the present invention, the said hydroxyl alkyl primary amine is monoethanolamine (MEA).

In accordance with one of the embodiments of the present invention, the said alkyl primary amine is octyl amine (OA).

In accordance with one of the embodiments of the present invention, the said alkyl secondary amine is dibutyl amine (DBA).

It has been found that when composition of present invention comprises one or more of said amines, the efficiency of nitroxide compounds to control and inhibit polymerization of aromatic vinyl monomers including styrene is, surprisingly and unexpectedly, substantially improved to the acceptable level that's too at substantially reduced dosages of nitroxide compounds and that's too without aromatic nitro compounds, thereby making the composition of present invention relatively more economical and environment friendly.

In accordance with one of the embodiments of the present invention, the composition of present invention comprises:
  a) about 40 to about 99.75% by weight of I) said nitroxide (i.e. nitroxyl) compounds; and
  b) about 0.25 to about 60% by weight of II) said amines or mixture thereof.

In accordance with one of the preferred embodiments of the present invention, the composition of present invention is added to the stream containing aromatic vinyl monomers including styrene in an amount varying from about 0.01 ppm to about 2000 ppm, preferably from about 1 ppm to about 2000 ppm by weight of the stream of monomer including styrene.

In accordance with present invention, the nitroxide (or nitroxyl) compound is selected from the group comprising di-tert-butylnitroxyl, 1-oxyl-2,2,6,6-tetramethylpiperidine, 1-oxyl-2,2,6,6-tetramethylpiperidin-4-ol, 1-oxyl-2,2,6,6-tetramethylpiperidin-4-one, and derivatives thereof; and di-nitroxides and derivatives comprising bis(1-oxyl-2,2,6,6-tetramethylpiperidin-4-yl)sebacate, bis(1-oxyl-2,2,6,6-tetramethylpiperidin-4-yesuccinate, bis(1-oxyl-2,2,6,6-tetramethylpiperidin-4-yl)adipate, and mixture thereof.

In accordance with preferred embodiment of the present invention, the nitroxide (or nitroxyl) compound is selected from the group comprising bis(1-oxyl-2,2,6,6-tetramethyl-piperidin-4-yl)sebacate and 1 oxyl-2,2,6,6, tetramethylpiperidin-4-ol or 4-hydroxy-2,2,6,6-tetramethylpiperidin-1-oxyl (or 4 Hydroxy Tempo or 4-HT), and mixture thereof.

In accordance with most preferred embodiment of the present invention, the nitroxide (or nitroxyl) compound is 1 oxyl-2,2,6,6, tetramethylpiperidin-4-ol (or 4 Hydroxy Tempo or 4-HT).

In accordance with one of the preferred embodiments of the present invention, the present composition does not comprise aromatic nitro compound.

Accordingly, in another embodiment, the present invention also relates to method of using amine and nitroxide based additive composition of present invention described herein, a reference to which is drawn in entirety, to control and inhibit polymerization of aromatic vinyl monomers including styrene, wherein the stream comprising aromatic vinyl monomer including styrene is treated with an additive composition comprising one or more of nitroxides (i.e. nitroxyls) compounds and one or more of said amines.

In particular, in second embodiment, the present invention relates to a method of using additive composition of the present invention described herein, a reference to which is drawn in entirety, for controlling and inhibition of polymerization of aromatic vinyl monomers including styrene, wherein said composition comprises:
(a) one or more of nitroxides (i.e. nitroxyls) compounds; and characterized in that the said composition further comprises one or more of
(b) aliphatic amines selected from a group comprising tertiary amines, secondary amines and primary amines, preferably the amine is tertiary amine; and
said monomers are treated with said composition.

Accordingly, in this second embodiment, the present invention particularly relates to a method of using additive composition of the present invention described herein, a reference to which is drawn in entirety, for controlling and inhibition of polymerization of aromatic vinyl monomers including styrene, wherein said composition comprises:
(a) one or more of nitroxides (i.e. nitroxyls) compounds; and characterized in that the said composition further comprises one or more of
(b) tertiary amines; and
said monomers are treated with said composition.

Accordingly, in this second embodiment, the present invention also relates to a method of using additive composition of the present invention described herein, a reference to which is drawn in entirety, for controlling and inhibition of polymerization of aromatic vinyl monomers including styrene, wherein said composition comprises:
(a) one or more of nitroxides (i.e. nitroxyls) compounds; and characterized in that the said composition further comprises one or more of
(b) amines selected from a group consisting of primary amines and secondary amines; and
said monomers are treated with said composition.

It may be noted that the stream comprising aromatic vinyl monomers including styrene may be referred to as stream or monomers stream or as aromatic vinyl monomers stream.

In accordance with one of the embodiments of the present invention, the method of using said additive composition of the present invention comprises treating said monomers stream with about 0.01 ppm to about 2000 ppm, preferably from about 1 ppm to about 2000 ppm of said composition based on weight of monomers.

It may be noted that all the features of the composition of the present invention described herein, a reference to which is drawn in entirety, are deemed to have been included in present method of using said additive composition of the present invention.

Accordingly, in third embodiment, the present invention also relates to method for controlling and inhibiting polymerization of aromatic vinyl monomers including styrene by employing amine and nitroxide based additive composition of present invention described herein, a reference to which is drawn in entirety, wherein the stream comprising aromatic vinyl monomers including styrene is treated with an additive composition comprising one or more of nitroxides (i.e. nitroxyls) compounds and one or more of said amines.

In particular, in third embodiment, the present invention relates to a method for controlling and inhibition of polymerization of aromatic vinyl monomers including styrene by employing additive composition of the present invention described herein, a reference to which is drawn in entirety, wherein said composition comprises:
(a) one or more of nitroxides (i.e. nitroxyls) compounds; and characterized in that the said composition further comprises one or more of
(b) aliphatic amines selected from a group comprising tertiary amines, secondary amines and primary amines, preferably the amine is tertiary amine; and
said composition is added to said monomers.

Accordingly, in this third embodiment, the present invention particularly relates to a method for controlling and inhibition of polymerization of aromatic vinyl monomers including styrene by employing additive composition of the present invention described herein, a reference to which is drawn in entirety, wherein said composition comprises:
(a) one or more of nitroxides (i.e. nitroxyls) compounds; and characterized in that the said composition further comprises one or more of
(b) tertiary amines; and
said composition is added to said monomers.

Accordingly, in this third embodiment, the present invention also relates to a method for controlling and inhibition of polymerization of aromatic vinyl monomers including styrene by employing additive composition of the present invention described herein, a reference to which is drawn in entirety, wherein said composition comprises:
(a) one or more of nitroxides (i.e. nitroxyls) compounds; and characterized in that the said composition further comprises one or more of
(b) amines selected from a group consisting of primary amines and secondary amines; and
said composition is added to said monomers.

It may be noted that the stream comprising aromatic vinyl monomers including styrene may be referred to as stream or monomers stream or as aromatic vinyl monomers stream.

In accordance with one of the embodiments of the present invention, the method for controlling and inhibition of polymerization of aromatic vinyl monomers including styrene by employing said additive composition of the present invention comprises adding from about 0.01 ppm to about 2000 ppm, preferably from about 1 ppm to about 2000 ppm of said composition to the aromatic vinyl monomers stream including styrene based on weight of monomers.

It may be noted that all the features of the composition of the present invention described herein, a reference to which is drawn in entirety, are deemed to have been included in present method for controlling and inhibition of polymerization of aromatic vinyl monomers including styrene by employing said additive composition of the present invention.

In accordance with one of the embodiments of the present invention, the composition of present invention may be mixed with or added to the monomers stream containing aromatic vinyl monomers including styrene either before the stream enters into processing system or after the stream has entered into processing system, but preferably the composition is added to the stream containing aromatic vinyl monomers before its processing starts so that polymerization of aromatic vinyl monomers is avoided.

In accordance with one of the embodiments of the present invention, the nitroxide compounds and the amine compounds may be mixed with or added to the monomers stream individually or after mixing.

In accordance with one of the embodiments of the present invention, the present composition may be used in or employed with or added to monomers stream over a wide range of temperature varying from about 50 degree C. to about 180 degree C., preferably from about 60 degree C. to about 180 degree C.

The composition of present invention may be prepared in any known manner to prepare the compositions.

Accordingly, in fourth embodiment, the present invention also relates to method of preparing amine and nitroxide based additive composition of present invention described herein, a reference to which is drawn in entirety, for controlling and inhibiting polymerization of aromatic vinyl monomers including styrene, wherein the nitroxide and said amine compounds are added individually or after mixing.

In particular, in fourth embodiment, the present invention relates to a method for preparation of additive composition of the present invention described herein, a reference to which is drawn in entirety, for controlling and inhibition of polymerization of aromatic vinyl monomers including styrene, wherein the method comprises:
(A) mixing one or more of said nitroxide (i.e. nitroxyl) compounds,
characterized in that said nitroxide compound or mixture thereof is further mixed with one or more of
(B) aliphatic amines selected from a group comprising tertiary amines, secondary amines and primary amines, preferably the tertiary amines.

Accordingly, in this fourth embodiment, the present invention particularly relates to a method for preparation of additive composition of the present invention described herein, a reference to which is drawn in entirety, for controlling and inhibition of polymerization of aromatic vinyl monomers including styrene, wherein the method comprises:
(A) mixing one or more of said nitroxide (i.e. nitroxyl) compounds,
characterized in that said nitroxide compound or mixture thereof is further mixed with one or more of
(B) tertiary amines.

Accordingly, in this fourth embodiment, the present invention also relates to a method for preparation of additive composition of the present invention described herein, a reference to which is drawn in entirety, for controlling and inhibition of polymerization of aromatic vinyl monomers including styrene, wherein the method comprises:
(A) mixing one or more of said nitroxide (i.e. nitroxyl) compounds,
characterized in that said nitroxide compound or mixture thereof is further mixed with one or more of
(B) amines selected from a group consisting of primary amines and secondary amines.

It may be noted that the stream comprising aromatic vinyl monomers including styrene may be referred to as stream or monomers stream or as aromatic vinyl monomers stream.

It may be noted that all the features of the composition of the present invention described herein, a reference to which is drawn in entirety, are deemed to have been included in present method for preparation of additive composition of the present invention.

In one of the embodiments, the inventor has found that when present composition comprises any one of the amines selected from a group consisting of N,N,N',N'-Tetrakis(2-hydroxyethyl)ethylene-diamine) (THEED) and N,N,N',N'-Tetrakis(2-hydroxypropyl)ethylene-diamine) (Quadrol), then efficiency for controlling and inhibition of polymerization of aromatic vinyl monomers including styrene of the nitroxides is substantially improved, however, the efficiency improvement is not as substantial as for the composition comprising tris(2-hydroxypropyl)amine (TIPA). Therefore, as per most preferred embodiment of the present invention, tris(2-hydroxypropyl)amine (TIPA) is most preferred amine.

In another embodiment, the inventor has found that when present composition comprises any one of the amines selected from a group consisting of triethanolamine (TEA), Tris[N-butylamine] (TBA), monoethanolamine (MEA), octyl amine (OA), dibutyl amine (DBA), then efficiency for controlling and inhibition of polymerization of aromatic vinyl monomers including styrene of the nitroxides is improved, however, the efficiency improvement is not as substantial as for the composition comprising N,N,N',N'-Tetrakis(2-hydroxyethyl)ethylene-diamine) (THEED) or N,N,N',N'-Tetrakis(2-hydroxypropyl)ethylene-diamine) (Quadrol). Therefore, as per more preferred embodiment of the present invention, N,N,N',N'-Tetrakis(2-hydroxyethyl) ethylene-diamine) (THEED) and N,N,N',N'-Tetrakis(2-hydroxypropyl)ethylene-diamine) (Quadrol) are the more preferred amines. It has been found that dibutyl amine (DBA), surprisingly and unexpectedly, demonstrates better efficiency when used in compositions of dosages of about 200 ppm or more.

In still another embodiment, the inventor has found that when present composition comprises any one of the amines selected from a group consisting of N,N,disec-butyl-para-phenylene diamine (UOP5), ethylene diamine (EDA), tetraethylenepentamine (TEPA), dipropyl amine (DPA), or diethanol amine (DEA), then efficiency for controlling and inhibition of polymerization of aromatic vinyl monomers including styrene of the nitroxides is not improved. Therefore, in one embodiment, the present composition does not comprise any one of the amines selected from a group consisting of N,N,disec-butyl-para-phenylene diamine (UOP5), ethylene diamine (EDA), tetraethylenepentamine (TEPA), dipropyl amine (DPA), or diethanol amine (DEA).

It may be noted that some of these amines result in very marginal improvement in efficiency of nitroxides, but same is not commercially viable.

EXAMPLES

Further advantages and embodiments of the present invention will become more apparent from the following examples.

The present invention is now described with the help of following examples, which are not intended to limit scope of the present invention, but have been incorporated to illustrate mode and best mode of performing the present invention.

EXPERIMENTS

Main Experiment

In the following experiments, weighed amount of distilled styrene and additives were taken in a reactor (tube reactor or round bottom reactor) equipped with thermometer and nitrogen inlet and outlet. In these experiments a tube reactor was used without any mechanical stirrer, and enough $N_2$ flow was maintained to ensure proper agitation. The reactions were carried out at about 120° C. for about 2 hours. After the selected duration, the reactor was cooled to below about 10° C. by immersing in crushed ice. The contents of the reactor were then poured in a beaker. To this same beaker, approximately for 1.5-2 g chilled polymerization mixture, about 80 g methanol was used to precipitate the polymer formed in the styrene solution. The precipitate obtained was filtered, dried to remove methanol, and weighed.

The weight of the precipitate was reported as % polymer formed in following tables.

It may be noted that styrene was purified before use to remove the stabilizers.

In the following examples, the prior additive is a nitroxide, which is 1 oxyl-2,2,6,6, tetramethylpiperidin-4-ol (or 4 Hydroxy Tempo or 4-HT), which was taken in an amount of about 100, 200, 300, 500, or 1000 ppm by weight of styrene.

In the following examples, the present additive is a composition comprising nitroxide which is 1 oxyl-2,2,6,6, tetramethylpiperidin-4-ol (4 Hydroxy Tempo or 4-HT), and aliphatic tertiary amine, which is tri-isopropanol amine (TIPA) containing three hydroxyl groups, wherein from about 1 to about 20 ppm of TIPA is added to the weighed amount of nitroxide.

Experiment 1

The results of above Main Experiment when performed with 10 g of distilled styrene by heating to 120° C. for 2 h are provided in Table-I.

TABLE I

| Active Dosage of Prior Art Additive Composition (ppm) ↓ | % polymer formed with Prior art Additive | Active Dosage of Present Additive Composition (ppm) ↓ | % polymer formed with Present composition | Technical Effects of present composition |
|---|---|---|---|---|
| 100 ppm | 13.19 | 100 + 4 TIPA | 11.22 | Polymerization inhibition efficiency of nitroxide is improved, and % polymer formed is reduced substantially on addition of aliphatic tertiary amine in |
| | | 100 + 10 TIPA | 10.9 | |
| | | 100 + 15 TIPA | 6.28 | |
| | | 100 + 20 TIPA | 4.3 | |

TABLE I-continued

| Active Dosage of Prior Art Additive Composition (ppm) ↓ | % polymer formed with Prior art Additive | Active Dosage of Present Additive Composition (ppm) ↓ | % polymer formed with Present composition | Technical Effects of present composition |
|---|---|---|---|---|
| 200 ppm | 9.38 | 100 + 15 TIPA | 6.28 | nitroxide |
|  |  | 100 + 20 TIPA | 4.3 |  |
| 300 ppm | 5.1 | 100 + 20 TIPA | 4.3 |  |

It is understood from above Table-I that when just 4 ppm to 20 ppm of TIPA is added to 100 ppm of 4HT (prior art additive), the efficiency of 4-HT to control and inhibit polymerization of styrene is, surprisingly and unexpectedly, improved substantially.

It can also be seen from Table-I that polymerization of styrene is, surprisingly and unexpectedly, substantially reduced just on addition of 4 to 20 ppm of TIPA in 100 ppm of 4HT (prior art additive).

It may be noted, the % polymer formed with 100 ppm of 4-HT alone is substantially reduced from 13.19% to 11.22%, to 10.9%, to 6.28%, and to 4.3%, respectively when 4 ppm (3.85% of total composition), 10 ppm (9.09% of total composition), 15 ppm (13.04% of total composition) and 20 ppm (16.67% of total composition) of TIPA is added to 100 ppm of 4HT.

It can also be seen from Table-I that for composition comprising 100 ppm of 4HT and 15 ppm of TIPA (13.04% of TIPA of total composition), the % polymer formed is, surprisingly and unexpectedly, substantially less than % polymer formed with composition consisting of 200 ppm of 4-HT, meaning thereby, the present composition results in saving of half of dosage of 4-HT, and hence is economical and environment friendly.

It can also be seen from Table-I that for composition comprising 100 ppm of 4HT and 20 ppm of TIPA (16.67% of TIPA of total composition), the % polymer formed is, surprisingly and unexpectedly, substantially less than % polymer formed with composition consisting of 300 ppm of 4-HT, meaning thereby, the present composition results in saving of two-third of dosage of 4-HT, and hence, is economical and environment friendly.

Experiment 2

The results of above Main Experiment when performed with 10 g of distilled styrene by heating to 135° C. for 2 h are provided in Table-II.

TABLE II

| Active Dosage of Prior Art Additive Composition (ppm) ↓ | % polymer formed with Prior art Additive | Active Dosage of Present Additive Composition (ppm) ↓ | % polymer formed with Present composition | Technical Effects of present composition |
|---|---|---|---|---|
| 500 ppm | 16.7 | 500 + 5 TIPA | 6.45 | Polymerization inhibition efficiency of nitroxide is improved, and % polymer formed is reduced substantially on addition of aliphatic tertiary amine in nitroxide |
|  |  | 500 + 10 TIPA | 6.05 |  |
|  |  | 500 + 15 TIPA | 5.72 |  |
|  |  | 500 + 20 TIPA | 4.9 |  |
| 1000 ppm | 6.13 | 500 + 10 TIPA | 6.05 |  |
|  |  | 500 + 15 TIPA | 5.72 |  |
|  |  | 500 + 20 TIPA | 4.9 |  |

It is understood from above Table-II that when just 5 ppm to 20 ppm of TIPA is added even to higher dosage of 500 ppm of 4HT (prior art additive) and styrene stream with additive is treated even at higher temperature of 135° C., the efficiency of 4-HT to control and inhibit polymerization of styrene is, surprisingly and unexpectedly, improved substantially.

It can also be seen from Table-II that polymerization of styrene is, surprisingly and unexpectedly, substantially reduced just on addition of 5 to 20 ppm of TIPA in 500 ppm of 4HT (prior art additive).

It may be noted the % polymer formed with 500 ppm of 4-HT alone is substantially reduced even at higher temperature of about 135° C. from 16.7% to 6.45%, to 6.05%, to 5.72%, and to 4.9%, respectively when 5 ppm (just 0.99% of total composition), 10 ppm (just 1.96% of total composition), 15 ppm (just 2.91% of total composition) and 20 ppm (just 3.85% of total composition) of TIPA is added to 500 ppm of 4HT. The reduction achieved is even greater than about 3 times.

It can also be seen from Table-II that for composition comprising 500 ppm of 4HT and 10 ppm of TIPA (just 1.96% of TIPA of total composition), the % polymer formed is, surprisingly and unexpectedly, less than % polymer formed with composition consisting of 1000 ppm of 4-HT, meaning thereby, the present composition results in saving of half of dosage of 4-HT, and hence is economical and environment friendly.

Experiments 3 to 5

In the following examples, for above Main Experiment, the prior art additive composition is 4HT, which is taken in an amount of about 100, 200, and 300 ppm, and the present additive composition is a composition comprising 4HT being nitroxide, and additionally comprising TIPA, THEED, Quadrol, TEA, TBA, MEA, OA, DBA being amines of the present invention, which are taken in weight ratio of 99:1, 98:2, 95:5, 90:10, 85:15, 80:20, 70:30 and 50:50, the composition is made to 100, 200 and 300 ppm.

The inventor has further compared the results of present compositions with additive compositions comprising 4HT and amine selected from a group consisting of UOP5, EDA, TEPA, DPA, or DEA for comparative purposes.

As can be seen from data in Tables III, IV and V, with addition of about 1 to about 150 ppm of TIPA, THEED, Quadrol, TEA, TBA, MEA, OA or DBA to 4HT making total of 100, 200 and 300 ppm of the composition so as to have 4HT:Amine in a weight ratio of 99:1, 98:2, 95:5, 90:10, 85:15, 80:20, 70:30 and 50:50, the efficiency of prior art additive composition consisting of 4HT to control and inhibit polymerization of styrene is, surprisingly and unexpectedly, generally improved.

As can be seen, when present composition comprises any one of the amines selected from a group consisting of N,N,N',N'-Tetrakis(2-hydroxyethyl)ethylene-diamine) (THEED) and N,N,N',N'-Tetrakis(2-hydroxypropyl)ethylene-diamine) (Quadrol), then efficiency for controlling and inhibition of polymerization of aromatic vinyl monomers including styrene of the nitroxides is substantially improved, however, the improvement is not as substantial as for the composition comprising tris(2-hydroxypropyl)amine (TIPA). Therefore, as per most preferred embodiment of the present invention, tris(2-hydroxypropyl)amine (TIPA) is most preferred amine.

As can also be seen, when present composition comprises any one of the amines selected from a group consisting of triethanolamine (TEA), Tris[N-butylamine] (TBA), monoethanolamine (MEA), octyl amine (OA), dibutyl amine (DBA), then efficiency for controlling and inhibition of polymerization of aromatic vinyl monomers including styrene of the nitroxides is improved, however, the improvement is not as substantial as for the composition comprising N,N,N',N'-Tetrakis(2-hydroxyethyl)ethylene-diamine) (THEED) or N,N,N',N'-Tetrakis(2-hydroxypropyl)ethylene-diamine) (Quadrol). Therefore, as per more preferred embodiment of the present invention, N,N,N',N'-Tetrakis(2-hydroxyethyl)ethylene-diamine) (THEED) and N,N,N',N'-Tetrakis(2-hydroxypropyl)ethylene-diamine) (Quadrol) are the more preferred amines.

As can be seen, dibutyl amine (DBA), surprisingly and unexpectedly, demonstrates better efficiency when used in compositions of dosages of about 200 ppm or more.

As can also be seen, when the composition comprises any one of the comparative amines selected from a group consisting of N,N,disec-butyl-para-phenylene diamine (UOP5), ethylene diamine (EDA), tetraethylenepentamine (TEPA), dipropyl amine (DPA), or diethanol amine (DEA), then efficiency for controlling and inhibition of polymerization of aromatic vinyl monomers including styrene of the nitroxides is not improved. Therefore, in one embodiment, the present composition does not comprise any one of the amines selected from a group consisting of N,N,disec-butyl-para-phenylene diamine (UOP5), ethylene diamine (EDA), tetraethylenepentamine (TEPA), dipropyl amine (DPA), or diethanol amine (DEA). It may be noted that some of these amines result in very marginal improvement in efficiency of nitroxides, but same is not commercially viable.

It may be noted that, surprisingly and unexpectedly, with increase in concentration of amine, i.e. when about 20% or more of the amine is added to 4HT, the polymerization inhibition efficiency of present additive composition reduces marginally, the reasons for which are not know at present.

Accordingly, in view of above experimental data and analysis thereof, it can be concluded that only the additive compositions of the present invention comprising 4HT and amine selected from a group consisting of TIPA, THEED, Quadrol, TEA, TBA, MEA, OA and DBA, surprisingly and unexpectedly, result in improvement of control and polymerization inhibition efficiency of prior art additive composition consisting of 4HT, and these findings confirm synergistic effect of present compositions.

TABLE III

| Active Dosage Ratio of 4HT:Amine | Total Dosage (ppm) | Active Dosage 4HT + Amine | 4HT | 4HT/TIPA | 4HT/THEED | 4HT/Quadrol | 4HT/TEA | 4HT/MEA | 4HT/TBA | 4HT/Octyl amine | 4HT/DPA | 4HT/DEA | 4HT/UOP5 | 4HT/DBA | 4HT/EDA | 4HT/TEPA |
|---|---|---|---|---|---|---|---|---|---|---|---|---|---|---|---|---|
| 99:1 | 100 | 99 + 1 | 13.9 | 11.15 | 11.65 | 11.57 | 12.86 | 12.50 | 12.95 | 12.82 | 12.27 | 12.83 | 13.04 | 13.33 | 13.65 | 13.85 |
| 98:2 | 100 | 98 + 2 | 13.9 | 10.61 | 11.16 | 11.23 | 12.25 | 12.18 | 12.61 | 12.35 | 11.86 | 12.32 | 13.22 | 13.58 | 13.91 | 14.22 |
| 95:5 | 100 | 95 + 5 | 13.9 | 8.84 | 9.81 | 9.95 | 11.06 | 12.08 | 11.82 | 11.95 | 11.68 | 12.52 | 13.55 | 13.78 | 14.1 | 14.08 |
| 90:10 | 100 | 90 + 10 | 13.9 | 7.52 | 9.15 | 9.25 | 10.38 | 11.83 | 11.5 | 11.25 | 11.58 | 12.9 | 13.69 | 14.01 | 14.2 | 14.5 |
| 85:15 | 100 | 85 + 15 | 13.9 | 7.34 | 8.89 | 8.80 | 9.31 | 11.25 | 11.0 | 10.86 | 11.94 | 13.35 | 13.92 | 14.25 | 14.4 | 14.67 |
| 80:20 | 100 | 80 + 20 | 13.9 | 7.4 | 8.45 | 8.43 | 9.05 | 11.05 | 11.2 | 11.56 | 12.60 | 14.0 | 14.21 | 14.4 | 14.61 | 14.75 |
| 70:30 | 100 | 70 + 30 | 13.9 | 8.10 | 9.26 | 9.16 | 9.97 | 11.20 | 11.68 | 12.15 | 13.24 | 15.6 | 14.68 | 14.64 | 14.86 | 15.15 |
| 50:50 | 100 | 50 + 50 | 13.9 | 8.30 | 9.92 | 9.82 | 10.87 | 11.98 | 13.05 | 13.11 | 14.56 | 16.8 | 15.59 | 15.11 | 15.96 | 16.27 |

TABLE IV

| Active Dosage Ratio of 4HT:Amine | Total Dosage (ppm) | Active Dosage (ppm) of 4HT + Amine | 4HT | 4HT/ TIPA | 4HT/ THEED | 4HT/ Quadrol | 4HT/ TEA | 4HT/ MEA | 4HT/ DBA | 4HT/ TBA | 4HT/ Octyl amine | 4HT/ DPA | 4HT/ DEA | 4HT/ UOP5 | 4HT/ EDA | 4HT/ TEPA |
|---|---|---|---|---|---|---|---|---|---|---|---|---|---|---|---|---|
| 99:1 | 200 | 198 + 2 | 9.38 | 3.05 | 4.49 | 4.5 | 8.86 | 8.2 | 6.47 | 9.09 | 8.8 | 9.10 | 9.21 | 9.33 | 9.52 | 9.64 |
| 98:2 | 200 | 196 + 4 | 9.38 | 2.5 | 3.87 | 3.94 | 7.08 | 7.87 | 6.66 | 8.83 | 8.33 | 8.53 | 9.08 | 9.67 | 9.8 | 9.92 |
| 95:5 | 200 | 190 + 10 | 9.38 | 2.14 | 3.47 | 3.53 | 5.26 | 7.41 | 6.90 | 8.45 | 8.03 | 8.39 | 9.27 | 9.82 | 9.91 | 10.20 |
| 90:10 | 200 | 180 + 20 | 9.38 | 1.91 | 3.12 | 3.06 | 4.11 | 7.21 | 7.25 | 8.08 | 7.42 | 8.11 | 9.54 | 10.02 | 10.22 | 10.55 |
| 85:15 | 200 | 170 + 30 | 9.38 | 1.74 | 2.75 | 2.86 | 3.58 | 7.08 | 7.55 | 7.60 | 7.11 | 8.62 | 9.76 | 10.33 | 10.5 | 10.77 |
| 80:20 | 200 | 160 + 40 | 9.38 | 1.80 | 2.42 | 2.49 | 3.22 | 7.25 | 7.82 | 7.96 | 7.66 | 9.35 | 10.2 | 10.52 | 10.71 | 11.88 |
| 70:30 | 200 | 140 + 60 | 9.38 | 2.53 | 3.22 | 3.18 | 4.06 | 7.64 | 8.21 | 8.24 | 8.11 | 9.91 | 10.9 | 11.0 | 11.14 | 12.07 |
| 50:50 | 200 | 100 + 100 | 9.38 | 3.10 | 3.65 | 3.62 | 4.98 | 8.25 | 9.02 | 9.65 | 8.95 | 10.28 | 11.5 | 11.5 | 11.26 | 12.79 |

TABLE V

| Active Dosage Ratio of 4HT:Amine | Total Dosage, ppm | Active Dosage (ppm) of 4HT + Amine | 4HT | 4HT/ TIPA | 4HT/ THEED | 4HT/ Quadrol | 4HT/ TEA | 4HT/ MEA | 4HT/ TBA | 4HT/ Octyl amine | 4HT/ DBA | 4HT/ UOP5 | 4HT/ DEA | 4HT/ DPA | 4HT/ EDA | 4HT/ TEPA |
|---|---|---|---|---|---|---|---|---|---|---|---|---|---|---|---|---|
| 99:1 | 300 | 297 + 3 | 5.1 | 1.35 | 2.28 | 2.23 | 4.74 | 3.95 | 4.8 | 4.53 | 4.15 | 5.05 | 5.06 | 4.91 | 5.2 | 5.5 |
| 98:2 | 300 | 294 + 6 | 5.1 | 1.07 | 1.50 | 1.55 | 4.05 | 3.24 | 4.09 | 3.92 | 3.53 | 5.24 | 4.95 | 4.63 | 5.64 | 5.75 |
| 95:5 | 300 | 285 + 15 | 5.1 | 0.88 | 1.41 | 1.44 | 3.22 | 3.08 | 3.78 | 3.8 | 3.30 | 5.62 | 5.56 | 4.23 | 6.08 | 6.17 |
| 90:10 | 300 | 270 + 30 | 5.1 | 0.77 | 1.17 | 1.25 | 2.44 | 2.84 | 3.5 | 3.29 | 3.15 | 5.90 | 5.77 | 4.05 | 6.20 | 6.45 |
| 85:15 | 300 | 255 + 45 | 5.1 | 0.62 | 0.95 | 1.02 | 2.23 | 3.04 | 2.7 | 2.92 | 3.04 | 7.51 | 6.10 | 4.35 | 6.34 | 6.62 |
| 80:20 | 300 | 240 + 60 | 5.1 | 0.51 | 0.79 | 0.83 | 1.95 | 3.55 | 3.25 | 3.2 | 3.41 | 7.7 | 7.5 | 4.65 | 6.91 | 7.09 |
| 70:30 | 300 | 210 + 90 | 5.1 | 0.68 | 1.09 | 1.12 | 2.55 | 4.22 | 3.68 | 3.56 | 3.9 | 8.9 | 8.8 | 5.26 | 8.18 | 8.96 |
| 50:50 | 300 | 150 + 150 | 5.1 | 0.75 | 1.70 | 1.66 | 3.22 | 4.82 | 4.36 | 4.33 | 4.55 | 9.9 | 9.7 | 6.55 | 9.26 | 10.05 |

Experiment 6

The above Main Experiment was also carried out with round bottom reactor for prior art additive composition consisting of 4HT; and present additive composition comprising 4HT and TIPA, and it has been found that with addition of present amine additives, the efficiency of prior art additive composition to control and inhibit polymerization of styrene is, surprisingly and unexpectedly, generally improved even in round bottom reactor.

TABLE VI

| Composition | Dosage, active, ppm | % Polymer |
|---|---|---|
| 4HT | 100 | 13.27 |
| 4HT | 200 | 9.11 |
| 4HT | 300 | 6.79 |
| 4HT | 400 | 2.32 |
| 4HT + TIPA (90:10) | 100 | 10.17 |
| 4HT + TIPA (90:10) | 200 | 4.42 |
| 4HT + TIPA (95:5) | 200 | 5.15 |

The above experimental data confirms the synergistic effects, and the surprising and unexpected technical effects and advantages of the additive composition of the present invention over the prior art additive composition and comparative compositions.

All of above findings confirm synergistic, surprising and unexpected effects of present composition at lower as well as at higher temperatures.

All of above findings also confirm that there is successive increase in efficiency of prior art additive to control and inhibit polymerization of styrene.

All of above findings also confirm that present composition is capable of achieving far better efficiency to control and inhibit polymerization of styrene with same dosage of the prior art additive, meaning thereby, the present invention results in economical and environmental benefits.

Above experimental results confirm that presently provided composition is far superior than prior art additive, and hence, has technical advantages and surprising effects over the prior art additive.

It may be noted that the term "about" as employed herein is not intended to enlarge scope of claimed invention, but has been incorporated only to include experimental errors permissible in the field of the art.

The invention claimed is:

1. Additive composition for controlling and inhibiting polymerization of aromatic vinyl monomers including styrene comprising:
   (a) one or more nitroxide (i.e. nitroxyl) compounds; and
   (b) one or more aliphatic tertiary amines;
   wherein the one or more aliphatic tertiary amines comprise hydroxyl alkyl aliphatic tertiary amine, ethylene oxide treated aliphatic tertiary amine, propylene oxide treated aliphatic tertiary amine, tertiary alkyl amine, or a combination thereof; and
   wherein the composition does not comprise the amine selected from a group consisting of phenylene diamine, ethylene diamine (EDA), tetraethylenepentamine, dipropyl amine, and diethanol amine.

2. The additive composition as claimed in claim 1, wherein said hydroxyl alkyl aliphatic tertiary amine is tris(2-hydroxypropyl)amine (TIPA).

3. The additive composition as claimed in claim 1, wherein said ethylene oxide treated aliphatic tertiary amine is N,N,N',N'-Tetrakis (2-hydroxyethyl) ethylene-diamine (THEED).

4. The additive composition as claimed in claim 1, wherein said propylene oxide treated aliphatic tertiary amine is N,N,N',N'-Tetrakis (2-hydroxypropyl) ethylene-diamine (Quadrol).

5. The additive composition as claimed in claim 1, wherein said hydroxyl alkyl aliphatic tertiary amine is triethanolamine (TEA).

6. The additive composition as claimed in claim 1, wherein said tertiary alkyl amine is Tris[N-butylamine] (TBA).

7. The additive composition as claimed in claim 1, wherein said composition comprises:
   a) about 40 to about 99.75% by weight of I) said nitroxide (i.e. nitroxyl) compounds; and
   b) about 0.25 to about 60% by weight of II) said aliphatic tertiary amines, or a mixture thereof.

8. The additive composition as claimed in claim 1, wherein about 0.01 to about 2000 ppm of said composition is added to aromatic vinyl monomers stream based on weight of monomer.

9. The additive composition as claimed in claim 1, wherein said nitroxide (i.e. nitroxyl) compound comprises di-tert-butylnitroxyl, 1-oxyl-2,2,6,6-tetramethylpiperidine, 1-oxyl-2,2,6,6-tetramethylpiperidin-4-ol, 1-oxyl-2,2,6,6-tetramethylpiperidin-4-one, or derivatives thereof; or di-nitroxides or derivatives comprising bis(1-oxyl-2,2,6,6-tetramethylpiperidin-4-yl)sebacate, bis(1-oxyl-2,2,6,6-tetramethylpiperidin-4-yl)succinate, bis(1-oxyl-2,2,6,6-tetramethylpiperidin-4-yl)adipate, or a mixture thereof.

10. The additive composition as claimed in claim 1, wherein said composition does not comprise aromatic nitro compound.

11. A method for controlling and inhibiting polymerization of aromatic vinyl monomers including styrene by adding the additive composition as claimed in claim 1 to monomers stream, wherein said composition comprises:
   (a) one or more of nitroxide (i.e. nitroxyl) compounds; and
   (b) one or more said aliphatic tertiary amines; and
   said composition is added to said monomers.

12. The method as claimed in claim 11, wherein about 0.01 to about 2000 ppm of said composition is added to aromatic vinyl monomers stream based on weight of monomer.

13. A method of using the additive composition as claimed in claim 1 for controlling and inhibiting polymerization of aromatic vinyl monomers including styrene, wherein said composition comprises:
   (a) one or more nitroxide (i.e. nitroxyl) compounds; and
   (b) one or more said aliphatic tertiary amines,
   and said monomers are treated with said composition.

14. The method as claimed in claim 13, wherein said aromatic vinyl monomers stream is treated with about 0.01 to about 2000 ppm of said composition based on weight of monomer.

15. A method for preparing the additive composition as claimed in claim 1 for controlling and inhibiting polymerization of aromatic vinyl monomers including styrene, wherein the method comprises:
   (A) mixing one or more said nitroxide (i.e. nitroxyl) compounds,
   with
   (B) one or more said aliphatic tertiary amines.

16. The method as claimed in claim 15, wherein said one or more of nitroxide compounds, and said one or more aliphatic tertiary amines are added to monomer stream individually.

17. The method as claimed in claim 11, wherein said composition is used over a range of temperature varying from about 50 degree C. to about 180 degree C.

18. The method as claimed in claim 13, wherein said composition is used over a range of temperature varying from about 50 degree C. to about 180 degree C.

19. Additive composition for controlling and inhibiting polymerization of aromatic vinyl monomers including styrene comprising:
   (a) one or more nitroxide (i.e. nitroxyl) compounds; and
   (h) one or more aliphatic secondary amines;
   wherein the composition does not comprise the amine selected from a group consisting of phenylenediamine, ethylene diamine (EDA), tetraethylenepentamine, dipropyl amine, and diethanol amine.

20. The additive composition as claimed in claim 19, wherein said aliphatic secondary amine is dibutyl amine (DBA).

21. The additive composition as claimed in claim 19, wherein said composition comprises:
   a) about 40 to about 9935% by weight of I) said nitroxide (i.e. nitroxyl) compounds; and
   b) about 0.25 to about 60% by weight of II) said one or more aliphatic secondary amines, or a mixture thereof.

22. The additive composition as claimed in claim 19, wherein about 0.01 to about 2000 ppm of said composition is added to aromatic vinyl monomers stream based on weight of monomer.

23. The additive composition as claimed in claim 19, wherein said nitroxide (i.e. nitroxyl) compound comprises di-tert-butylnitroxyl, 1-oxyl-2,2,6,6-tetramethylpiperidine, 1-oxyl-2,2,6,6-tetramethylpiperidin-4-ol, 1-oxyl-2,2,6,6-tetramethylpiperidin-4-one, or derivatives thereof; or di-nitroxides or derivatives comprising bis(1-oxyl-2,2,6,6-tetramethylpiperidin-4-yl)sebacate, bis(1-ox tetramethylpiperidin-4-yl)succinate, bis(1-oxyl-2,2,6,6-tetramethylpiperidin-4-yl)adipate, or a mixture thereof.

24. The additive composition as claimed in claim 19, wherein said composition does not comprise an aromatic nitro compound.

25. A method for controlling and inhibiting polymerization of aromatic vinyl monomers including styrene by adding the additive composition as claimed in claim 19 to monomers stream, wherein said composition comprises:
   (a) one or more nitroxide (i.e. nitroxyl) compounds; and
   (b) one or more said aliphatic secondary amines; and
   said composition is added to said monomers.

26. The method as claimed in claim 25, wherein about 0.01 to about 2000 ppm of said composition is added to aromatic vinyl monomers stream based on weight of monomer.

27. A method of using the additive composition as claimed in claim 19 for controlling and inhibiting polymerization of aromatic vinyl monomers including styrene, wherein said composition comprises:
   (a) one or more nitroxide (i.e. nitroxyl) compounds; and
   (b) one or more said aliphatic secondary amines,
   and said monomers are treated with said composition.

28. The method as claimed in claim 27, wherein said aromatic vinyl monomers stream is treated with about 0.01 to about 2000 ppm of said composition based on weight of monomer.

29. A method for preparing the additive composition as claimed in claim 19 for controlling and inhibiting polymerization of aromatic vinyl monomers including styrene, wherein the method comprises:
   (A) mixing one or more said nitroxide (i.e. nitroxyl) compounds with
   (B) one or more said aliphatic secondary amines.

30. The method as claimed in claim 29, wherein said one or more nitroxide compounds, and said one or more aliphatic secondary amines are added to monomer stream individually.

31. The method as claimed in claim 25, wherein said composition is used over a range of temperature varying from about 50 degree C. to about 180 degree C.

32. The method as claimed in claim 27, wherein said composition is used over a range of temperature varying from about 50 degree C. to about 180 degree C.

33. A composition comprising:
(i) aromatic vinyl monomers including styrene, and
(ii) an additive composition,
wherein the additive composition comprises:
(a) one or more nitroxide (i.e. nitroxyl) compounds; and
(b) one or more aliphatic tertiary amines;
wherein the one or more aliphatic tertiary amines comprise hydroxyl alkyl aliphatic tertiary amine, ethylene oxide treated aliphatic tertiary amine, propylene oxide treated aliphatic tertiary amine, tertiary alkyl amine, or a combination thereof; and
wherein the composition does not comprise the amine selected from a group consisting of phenylene diamine, ethylene diamine (EDA), tetraethylenepentamine, dipropyl amine, and diethanol amine.

* * * * *

UNITED STATES PATENT AND TRADEMARK OFFICE
CERTIFICATE OF CORRECTION

PATENT NO. : 9,725,649 B2
APPLICATION NO. : 14/362047
DATED : August 8, 2017
INVENTOR(S) : Mahesh Subramaniyam Page 1 of 1

It is certified that error appears in the above-identified patent and that said Letters Patent is hereby corrected as shown below:

In the Claims

Claim 21, Column 18, Line 19, replace "9935%" with --99.75%--

Claim 23, Column 18, Lines 33-34, replace "bis(1-ox tetramethylpiperidin-4-yl)succinate," with --bis(1-oxyl-2,2,6,6-tetramethylpiperidin-4-yl)succinate,--

Signed and Sealed this
Nineteenth Day of June, 2018

Andrei Iancu
*Director of the United States Patent and Trademark Office*